(12) United States Patent
Aga et al.

(10) Patent No.: US 12,742,765 B2
(45) Date of Patent: Sep. 22, 2026

(54) METHOD AND SYSTEMS FOR MONITORING AND MEASURING THE AMOUNT OF A GAS DISSOLVED IN A LIQUID

(71) Applicant: Searas AS, Bergen (NO)

(72) Inventors: Morten Aga, Bergen (NO); Eldar Lien, Bergen (NO); Vincent Martinez, Bergen (NO); Jan Vidar Nordstrand, Oslo (NO); Geir Valsvik, Laksevåg (NO)

(73) Assignee: SEARAS AS, Bergen (NO)

( * ) Notice: Subject to any disclaimer, the term of this patent is extended or adjusted under 35 U.S.C. 154(b) by 961 days.

(21) Appl. No.: 17/775,708

(22) PCT Filed: Nov. 13, 2020

(86) PCT No.: PCT/NO2020/050280
§ 371 (c)(1),
(2) Date: May 10, 2022

(87) PCT Pub. No.: WO2021/096369
PCT Pub. Date: May 20, 2021

(65) Prior Publication Data

US 2022/0404327 A1 Dec. 22, 2022

(30) Foreign Application Priority Data

Nov. 14, 2019 (NO) .................................... 20191352

(51) Int. Cl.
*G01N 33/18* (2006.01)
*B01D 19/00* (2006.01)
*G01N 33/00* (2006.01)
*G01P 5/06* (2006.01)

(52) U.S. Cl.
CPC ......... *G01N 33/18* (2013.01); *B01D 19/0073* (2013.01); *G01N 33/0044* (2013.01); *G01P 5/06* (2013.01); *G01N 33/0036* (2013.01); *G01N 33/004* (2013.01); *G01N 33/0054* (2013.01)

(58) Field of Classification Search
CPC .... A01K 63/042; G01N 1/14; G01N 33/0036; G01N 33/004; G01N 33/0044; G01N 33/0054; G01N 33/18; B01D 19/0073; G01P 5/06
See application file for complete search history.

(56) References Cited

FOREIGN PATENT DOCUMENTS

KR 101051367 B1 * 7/2011 ...... B01F 23/237612
WO WO-2019183411 A1 * 9/2019 ........... G01N 1/4022

OTHER PUBLICATIONS

Espacenet English Translation of KR101051367B1. (Year: 2011).*

* cited by examiner

*Primary Examiner* — Kathryn Elizabeth Limbaugh
(74) *Attorney, Agent, or Firm* — Flener IP & Business Law

(57) ABSTRACT

A method and system for measuring an amount of a gas dissolved in a liquid is described, in which the liquid is transferred to an equilibrator and in which the amount of the various gases is measured in the gas phase of the equilibrator and that a calculation of the amount of gas which is dissolved in the liquid is carried out.

15 Claims, 6 Drawing Sheets

METHOD AND SYSTEMS FOR MONITORING AND MEASURING THE AMOUNT OF A GAS DISSOLVED IN A LIQUID

FIELD OF THE INVENTION

The present invention relates to a method and system for measuring the amount of a gas dissolved in a liquid. In particular, the method is intended for measuring the amount of hydrogen sulphide gas ($H_2S$) dissolved in water.

BACKGROUND OF THE INVENTION

Fish farming has become a major industry, and in some fish farm installations, the formation of hydrogen sulphide in the water the fish is farmed in has led to significant problems. In particular, this has proven to be a problem in so-called RAS facilities where most of the water is recycled back to where the fish are farmed.

It has been shown that hydrogen sulphide is formed when there is sludge in the installations and oxygen-poor conditions will be established in different locations. Sulphate reducing bacteria will then convert sulphide to hydrogen sulphide. Seawater contains much larger amounts of sulphate than freshwater and the problems with the formation of hydrogen sulphate are therefore larger in fish farming installations using seawater. Hydrogen sulphide is soluble in water and a certain amount of hydrogen sulphide gas will be dissolved in the water where you find the fish. There are today no good practical measuring methods to measure low concentrations of hydrogen sulphide in a liquid.

DESCRIPTION OF PRIOR ART

Today there are sensors for measuring $H_2S$ in freshwater. These are used, for example, for analysis of drinking water. In seawater it has only come into use lately because there is a need to measure $H_2S$ and then particularly in RAS facilities for marine fish species such as salmon. $H_2S$ is highly toxic and easily soluble in water. Salt water contains 2700 mg sulphate per litre against 2.2 mg/litre for fresh water.

Sulfate-reducing bacteria are anaerobic bacteria that form $H_2S$. This happens in areas of the fishing vessel or water treatment system where there is poor water circulation. It also occurs in the biofilter if anaerobic conditions occur. In a heterotrophic biofilm, there will also be anaerobic conditions. Small amounts of $H_2S$ are produced here, and therefore there will always be a certain background level of $H_2S$ in all RAS facilities. This level is low, with up to 100 ng/litre and is therefore difficult to measure in water. The sensors are also very exposed to the corrosive seawater environment.

There are currently methods for measuring $H_2S$ in the range 1000-50000 ng/litre. This instrumentation is very expensive, and it is of interest to find solutions to be able to monitor concentrations of $H_2S$ even below 1000 ng/litre to get early warning that things are starting to happen in the installation.

Objects of the Present Invention

It is an object of the present invention to provide a method and system for measuring the amount of hydrogen sulphide in a liquid. An object is in the context to be able to measure a relative change in the amount of hydrogen sulphide in liquid, such as an increase or decrease in the amount of hydrogen sulphide in the liquid.

It is also an object to be able to measure other gases that are dissolved in the liquid.

Furthermore, it is an object of the invention to be able to measure hydrogen sulphide and/or other gases dissolved in any type of liquid. Thus, it is expedient to use the method for measuring hydrogen sulphide in liquid in a fish farm installation, but the method can also be used for other liquids, such as drinking water, treatment plants, etc.

It is also an object of the present invention to provide a system for carrying out the method of measuring hydrogen sulphide in a liquid.

It is also an object of the invention to provide a solution which can measure low concentrations of $H_2S$ in a liquid, i.e., a method which is more sensitive than the methods which are available today.

SUMMARY OF THE INVENTION

The present invention relates, in a first aspect, to a system for determining the amount of a gas dissolved in a liquid, characterised in that the system comprises means for continuously supplying said liquid to an equilibrator set up for adjusting the equilibrium between gases in a gas phase and liquid phase, and where gases from the gas phase in a closed gas volume are put into contact with the liquid phase, and where a sensor device measures the amount of gas in the gas phase.

In one embodiment the system is comprised of a gas conveyor arranged to effect circulation of gases from the gas phase to the liquid phase.

In one embodiment the equilibrator has an outlet with a water trap to regulate the liquid level in the equilibrator.

In one embodiment the sensor device measures the amount of gases directly in the gas phase (**80*a***) in the equilibrator.

In one embodiment gases from the gas phase are circulated in a closed circuit through the liquid phase.

In one embodiment the system is comprised of a gas conveyor which transports gases in a closed circuit from the gas phase to the liquid phase.

In one embodiment the gas conveyor is comprised of a pump and a pipeline for the transport of gases from the gas phase to the liquid phase.

In one embodiment the system is comprised of a closed loop and that gases from the gas phase are transported by a gas conveyor to the liquid phase via this loop, and that a sensor device is arranged in the loop and measures the amount of one or more gases in the gas phase.

In one embodiment gas from the gas phase is passed in a closed circuit via a sensor device for measuring the amount of a given gas.

In one embodiment the gas supply unit is a hose equipped with an air pump to collect gas from the gas phase and supply it to the liquid phase.

In one embodiment the gas conveyor is an ejector.

In one embodiment liquid is fed via a pump and pipelines to the top of the equilibrator and the ejector arranged in the liquid phase of the equilibrator, and that gases from the gas phase are sucked into the ejector via a pipeline.

In one embodiment a foam dampener in the gas phase is arranged in the equilibrator.

In one embodiment the foam dampener is arranged in the equilibrator so that there is a gas phase above the foam dampener.

In one embodiment the sensor device gases are sucked from the gas phase under the foam dampener.

In one embodiment gases are returned from the sensor device in return to the equilibrator via the gas phase above the foam dampener.

In one embodiment the liquid is supplied to the equilibrator via a nozzle, arranged to spread the water over the cross section of the equilibrator.

In one embodiment the gas conveyor is a diffuser.

In one embodiment gases from the gas phase are led via a pump from the foam dampener to the diffuser.

In one embodiment the equilibrator is arranged in the main horizontally and gases are circulated in a closed circuit through the gas phase in the equilibrator with the help of a pump or propeller.

In one embodiment the sensor device is connected to the closed circuit.

In one embodiment the liquid is transferred to the equilibrator via nozzles and is fed to the end edge of the equilibrator where it flows out through a pipeline with a water lock.

In one embodiment the measurements of the amount of gas are calibrated with measurements of a gas mixture, such as air, with a known gas composition.

In one embodiment the calibration takes place in a closed circuit equipped with valves, and that the calibration is performed automatically at given times.

In one embodiment the liquid which is supplied to the equilibrator is brought from a separate container.

In a second aspect the present invention relates to a method for determining the amount of a gas dissolved in a liquid, characterised in that the liquid is continuously supplied in a closed circuit to an equilibrator set up to adjust an equilibrium between the gases in a gas phase and the gases dissolved in a liquid phase in the equilibrator, and where gases from the gas phase in a closed gas volume are brought into contact with the liquid phase, and that a sensor device measures the amount of one or more gases in the gas phase.

In one embodiment the gas conveyor causes gas to circulate from the gas phase to the liquid phase.

In one embodiment the gas conveyor is a pump and a pipeline for transporting gases from the gas phase to the liquid phase.

In one embodiment gases are transported from the gas phase by a gas conveyor to the liquid phase in a closed loop, and that a sensor device is arranged in the loop and measures the amount of one or more gases in the gas phase.

In one embodiment gas from the gas phase is passed in a closed circuit via a sensor device for measuring the amount of a given gas.

In one embodiment the gas conveyor is a hose equipped with an air pump to collect gas from the gas phase and supply it to the liquid phase.

In one embodiment the gas conveyor is an ejector.

In one embodiment the gas conveyor is a diffuser.

In one embodiment the sensor device measures the amount of one or more gases selected from hydrogen sulphide, carbon dioxide, oxygen and ammonia, among others.

In one embodiment said gas is hydrogen sulphide.

In one embodiment the average throughflow velocity and the amount of liquid through the equilibrator is measured or estimated so that the absolute amount of gas dissolved in the liquid can be estimated.

In one embodiment the gas conveyor generates microbubbles to the liquid phase.

In one embodiment the liquid is continuously transferred from a first container to the equilibrator.

In one embodiment a system is arranged in several places in fish farm installations.

In one embodiment the system is arranged to measure the amounts of gas in liquid which is let into the farming tank.

In one embodiment the system is set up to measure the amount of gas emitted from the plant via the $CO_2$ stripper.

In one embodiment the system is set up between one or more, or all of the modules in a fish farm installation, such as an RAS facility.

In one embodiment the measurements are performed in real time and a transmitter unit on the sensor device sends data to a control unit.

In one embodiment the system is set up with valves so that one can, using programmable intervals, be able to insert a calibration gas with known concentrations to control the drift of the sensors.

DESCRIPTION OF THE FIGURES

Preferred embodiments of the invention shall be discussed in more detail in the following with reference to the accompanying figures, in which.

Description of Preferred Embodiments of the Invention

As mentioned above, there are no solutions to be able to measure $H_2S$ in a solution that is sufficiently sensitive to, for example, detect levels of $H_2S$ that are harmful to fish.

This problem has been sought to be solved by the present invention by transferring the liquid to an equilibrator in a continuous flow. The equilibrator is a container in which an equilibrium is set between gases in the liquid phase and in the gas phase. Gases from the gas phase are then put in contact with the liquid phase so that an efficient exchange of gases between the gas and liquid phases is achieved.

In one embodiment this is solved by the gases passing through the sensor box also being circulated in a closed circuit through the water flowing through the equilibrator. There will then be an equilibrium between water and the gas above the water surface so that the gases in this gas phase at all times reflect the content of gases in the liquid phase. The sensors therefore measure gases that are in equilibrium with the liquid and are therefore not directly exposed to the liquid with all the problems this entails in the form of fouling and maintenance and service life and accuracy of the sensors.

Figure 1:
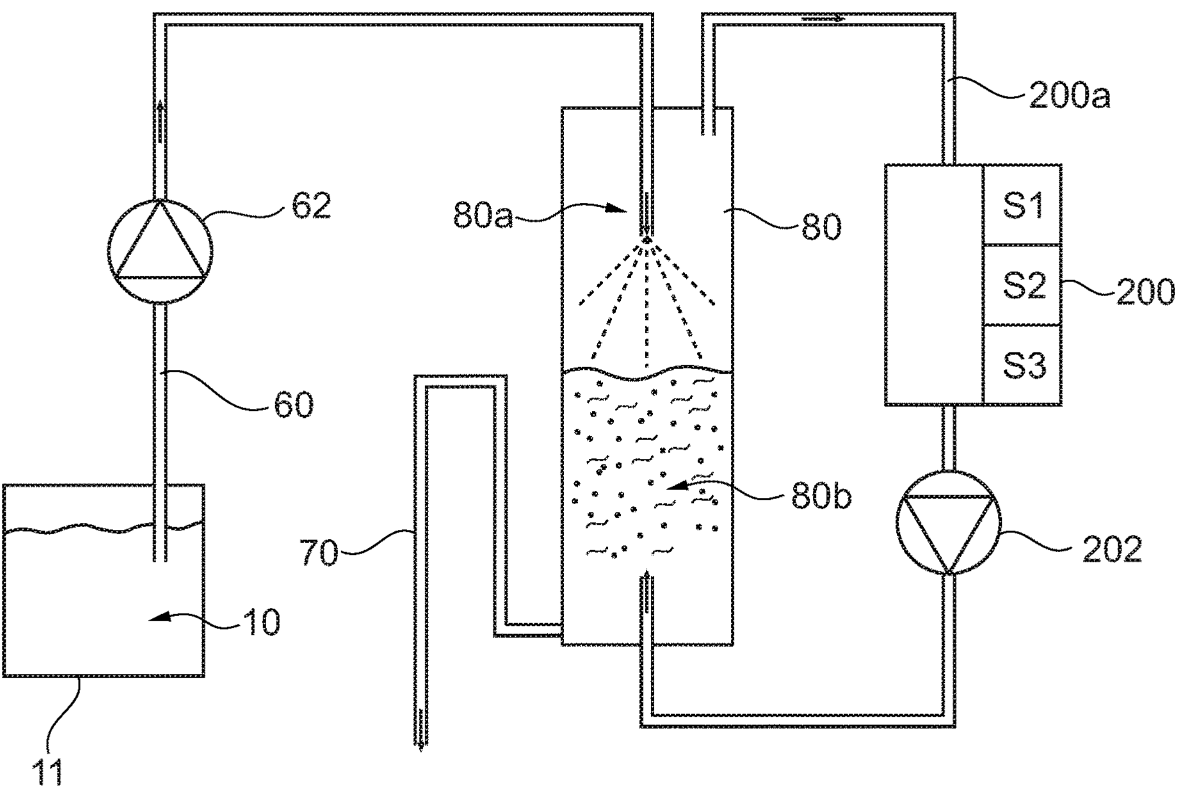
FIG. 1 shows schematically a system for measuring the concentration or amount of a gas in a liquid. The liquid is transferred in a continuous flow to an equilibrator, and the amount of gas is measured in the gas phase in this equilibrator.

FIG. 1 shows schematically a general embodiment of the invention in which the concentration or amount of a given gas dissolved in a liquid 10 contained in a container 11 is to be measured. The container 11 can, for instance, be a watertight net cage for the farming of fish or the tank in a RAS facility.

Since there are no sensors that can measure low $H_2S$ concentrations in the liquid 10, especially when this liquid 10 is salt water, then the liquid 10 is transferred in a continuous flow with the help of a pump 62 via the pipeline 60 to an equilibrator 80. In FIG. 1 it is shown that the liquid is supplied in the upper part of the equilibrator, but the liquid 10 can in principle be supplied everywhere in the equilibrator 80, also to the liquid phase 80*b* at the bottom of the equilibrator 80.

From the equilibrator 80 runs an outlet 70 arranged to regulate the water level in the equilibrator 80.

In the equilibrator 80, an equilibrium between the liquid phase 80*b* and the gas or air phase 80*a* is set such that the amount of a given gas in the gas phase 80*a* is correlated to the amount of this gas in the liquid phase 80*b*. As the liquid 10 flows continuously from the container 11 to the equilibrator 80, and since the system is closed, the content of a given gas in the gas phase 80*a* is correlated to the amount of this gas dissolved in the liquid 10 in container 11. Then, one can for measurement of the gas content in 80*a* estimate the actual gas content in the liquid 10 in container 11.

This solution represents a completely new principle for measuring the amount or concentration of a gas in a liquid in that the liquid flows through the equilibrator.

Gases from the gas phase 80*a* are circulated in a closed circuit which is in contact with or flows through the liquid phase 80*b*, and an equilibrium is set between gases in the liquid phase 80*b* and the gas phase 80*a*. The measurement of gas is performed in the gas phase 80*a* but reflects amounts of gas in the liquid phase 80*b*. Thereby, this prevents the sensors from being in contact with the liquid 10. This principle can be used to measure any gas but is particularly suitable for monitoring gases which are difficult to measure directly in the liquid 10.

The system and method according to the invention are specially developed to measure low concentrations of $H_2S$ but can also be used on other gases and also when the gas amounts dissolved in the liquid 10 are larger.

In the simplest embodiment of the invention the sensors 200 are placed directly into the gas phase 80*a*. This solution is not shown in the figures. If the liquid is leaked/spread into the equilibrator 80, no additional means are required to transport gas from the gas phase 80*a* to the liquid phase 80*b*. However, it is often preferable to have other means arranged in the equilibrator 80 to transfer gases from the gas phase 80*a* to 80*b*. Such means are shown in the FIGS. 2-4.

FIG. 1 shows a more preferred solution for measuring the concentration and amount of the gases. A pipeline 200*a* carries the gases by means of a pump 202 from the gas phase 80*a* via a sensor device 200, and back to the equilibrator 80, preferably via the liquid phase 80*b* in the equilibrator 80. This circuit is closed and no gases or air are supplied from outside as the gases only circulate from the gas phase 80*a* to the liquid phase 80*b*, via the sensor device 200. This circulation of gases is favourable for setting the equilibrium between gases in the liquid phase 80*b* and the gas phase 80*a*, and the measurements of a given gas become most accurate when there is near equilibrium in the equilibrator 80.

It is schematically stated in the sensor device 200 that it is comprised of sensors S1, S2 and S3, and these can, for instance, be sensors for measuring $H_2S$, $CO_2$ and $O_2$, respectively, which are important gases to monitor in an RAS facility.

Figure 2:
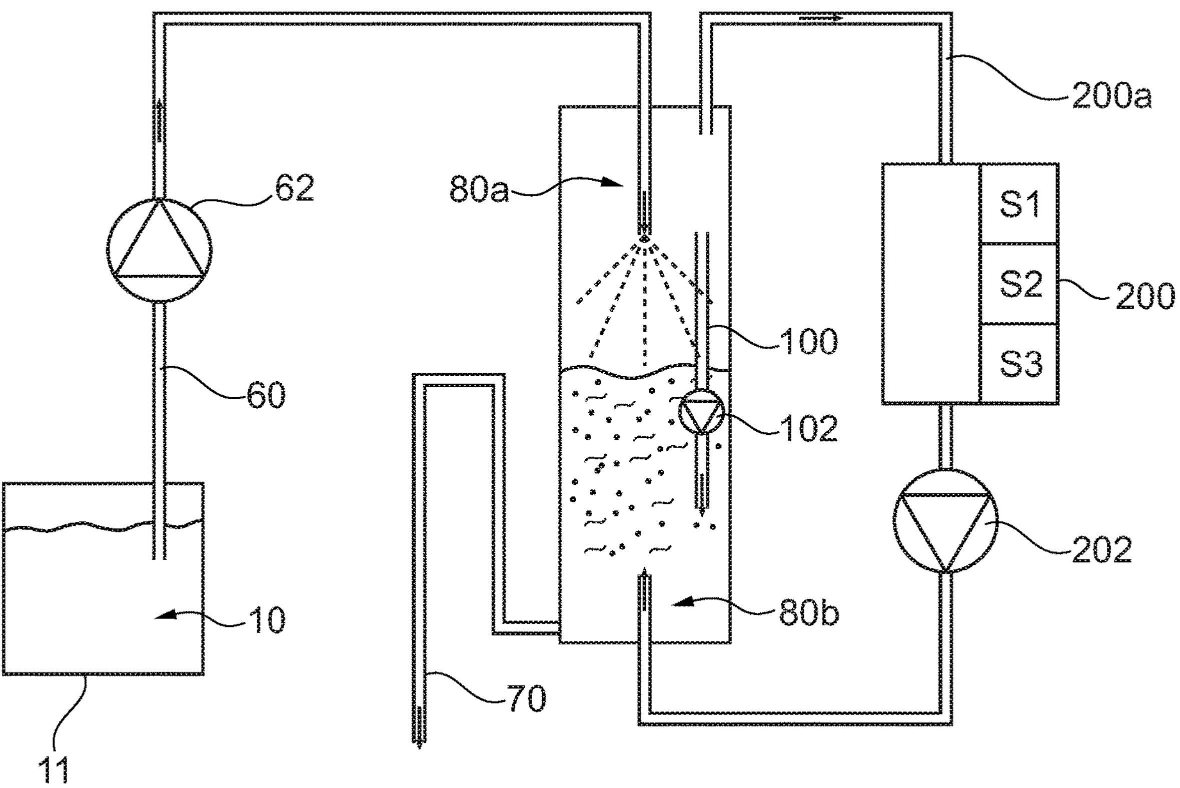
FIG. 2 shows the same solution as FIG. 1, but where there is also a gas conveyor for transporting gases from the gas phase in the equilibrator to the liquid phase in the equilibrator.

FIG. 2 shows in principle the same solution as in FIG. 1, but where an additional gas conveyor 100 is inserted to improve the exchange of gases between the gas phase 80*a* and the liquid phase 80*b*, i.e., so that the equilibrium in the equilibrator 80 adjusts faster. The gas conveyor 100 in FIG. 2 is a pipeline that runs from the gas phase 80*a* to the liquid phase 80*b* and which is fitted with a pump 102 such that gas can be transported from the gas phase 80*a* to the liquid phase 80*b*. The circuit is closed and there is no gas supplied to the system, only a transfer from 80a to 80*b* to improve the exchange of gases between the two phases.

In FIG. 2, this gas conveyor 100 is schematically shown inside the equilibrator 80, but in an alternative embodiment it is arranged on the outside of the equilibrator 80 but where the pipelines extend through the equilibrator 80 so that gases can be transferred from 80a to 80*b*.

Experiments have shown that it is beneficial that the gases that are discharged from the gas conveyor in the liquid phase 80*b* are in the form of small gas bubbles, preferably as microbubbles. These have a large surface area in relation to volume, i.e., a relatively large interface between liquid and gas, and this causes a quick exchange of gases between 80a and 80b, and a quick adjustment of the equilibrium in the equilibrator 80.

Figures 3, 4:
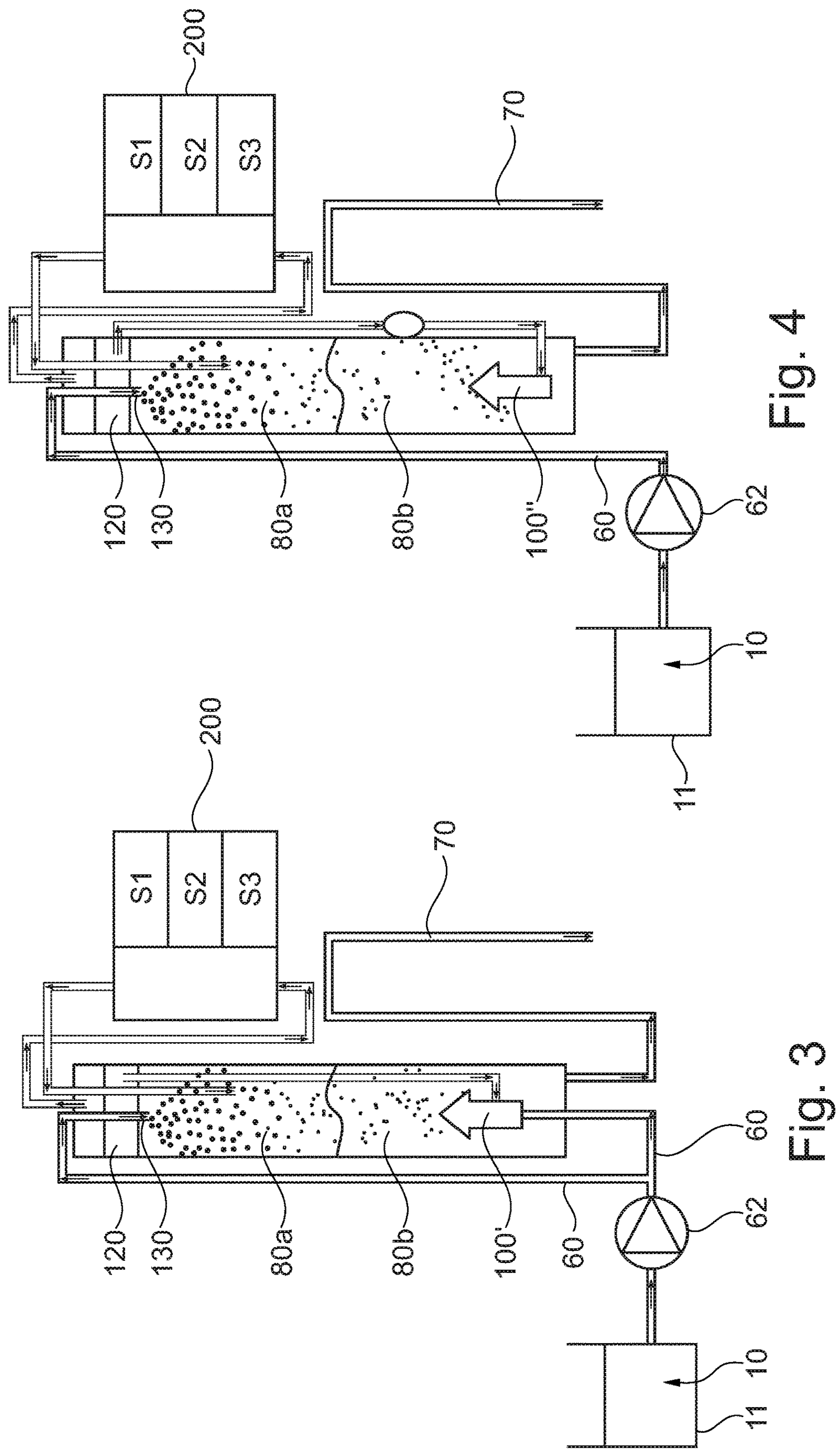
FIG. 3 show schematically a solution where the gas conveyor is an ejector.
FIG. 4 shows schematically a solution where the gas conveyor is a diffuser.

FIG. 3 (FIG. 6) is an embodiment of the invention using an ejector 100' to generate gas bubbles in the liquid phase 80*b*. Liquid 10 from container 11 is fed via pump 62 and pipelines 60 to both the top of the equilibrator 80 and to an ejector 100' placed in the liquid phase 80*b* of the equilibrator. Gases from the gas phase 80*a* are sucked into the ejector 100' via the pipeline 100.

FIG. 3 also shows a couple of other elements that improve the system and the method. When using ejector 100', depending on the type of liquid 10, some foam is generated. FIG. 3 therefore shows a foam dampener 120 arranged in the equilibrator 80, which reduces the amount of foam in the gas phase 80*a*. It is further preferred that the liquid 10 from vessel 11 is led via this foam dampener 120 to the equilibrator 80.

The foam dampener 120 can be placed at different levels in the equilibrator 80. Above the foam dampener 120 there is a gas space, where one can, for example, suck gases to the sensor box 200. Foam should not come up into this space. Gases returning from the sensor box 200 pass through foam dampener 120 so that these gases interact with gases coming from the ejector 100'.

If foam comes up into the foam dampener 120 then it is sucked down again to the ejector 100' together with the gases. When foam is sucked down to the ejector 100', this will not function well and thus also generate less foam. In this way we prevent foam from coming over the foam dampener 120.

The foam dampener 120 has openings 120*a* which allow gases to circulate through it, but higher density foam is sucked into the return and down to the ejector 100'.

FIG. 3 also shows that liquid 10 coming from container 11 is dispersed via a nozzle 130. This nozzle 130 distributes the water throughout the entire cross section of the equilibrator 80 and provides a good gas exchange between the gas phase 80*a* and the liquid phase 80*b*. In further embodiments it is shown that this nozzle provides such an efficient gas exchange that it is not necessary to use an ejector or diffuser, i.e., the solution with nozzle 130 is used together with the embodiments that are shown in FIGS. 1 and 2.

FIG. 4 shows a similar embodiment, but where the ejector 100' is replaced with a diffuser 100" (effervescence stone) which takes gases from the gas phase 80*a* through a pump 102" from the foam dampener 120 and to a diffuser 100" which is placed in the liquid phase 80*b*. This solution with diffuser 100" can also be realised without the form dampener 120 and nozzle 130, although these solutions are not shown in FIG. 4.

Figure 5:
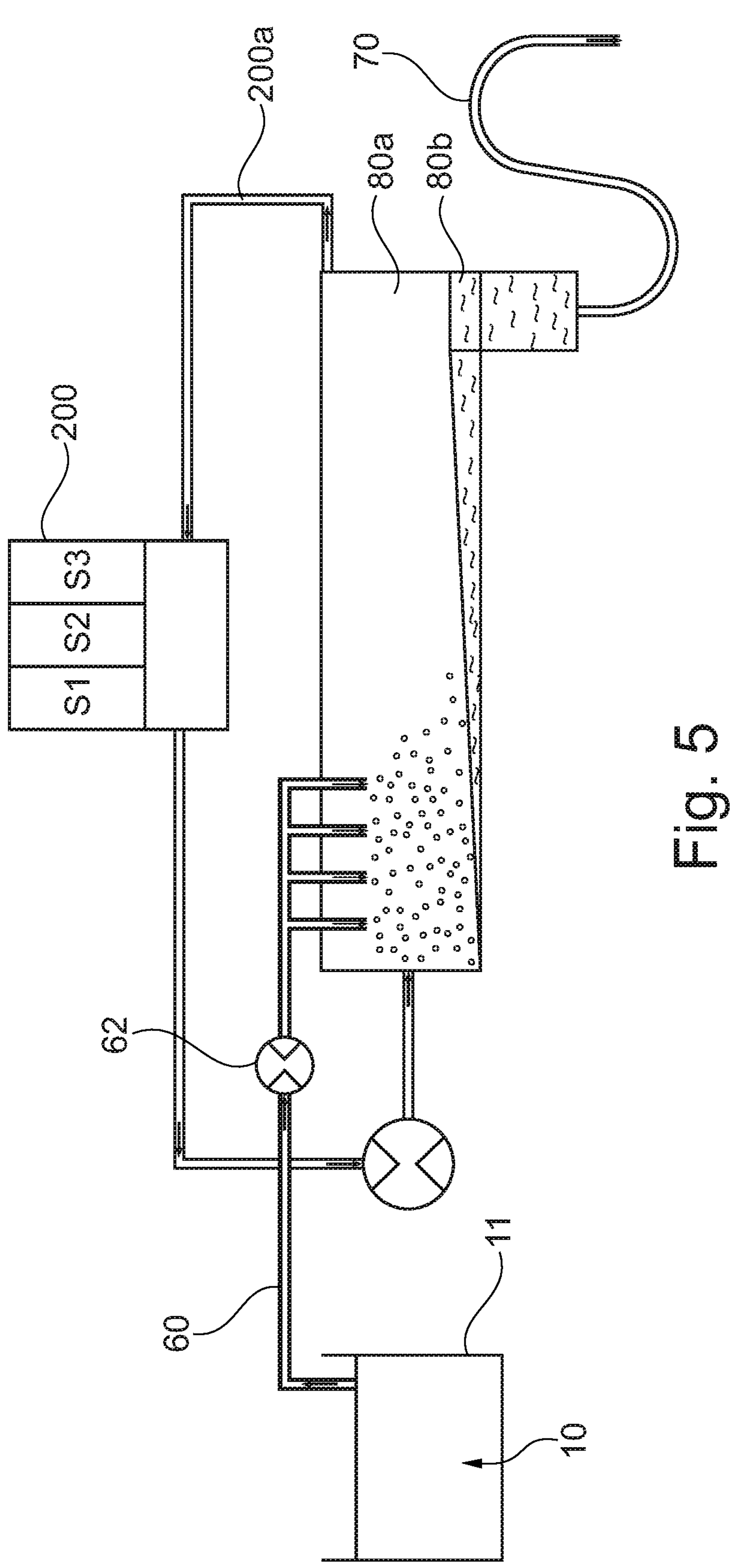
FIG. 5 shows schematically a system where the equilibrator is arranged horizontally.

FIG. 5 shows a solution where the equilibrator 80 is arranged horizontally and gases are circulated in a closed circuit through the gas phase 80*a* in the equilibrator 80 with the help of a pump or propeller. The sensor device 200 can also be connected to this closed circuit. The liquid 10 is transferred from the container 11 and is discharged through shower heads 130' and led to the end edge of the equilibrator 80 where it flows out through the pipeline 70 with a water trap which regulates the height of the water level in the equilibrator 80.

Figure 6:
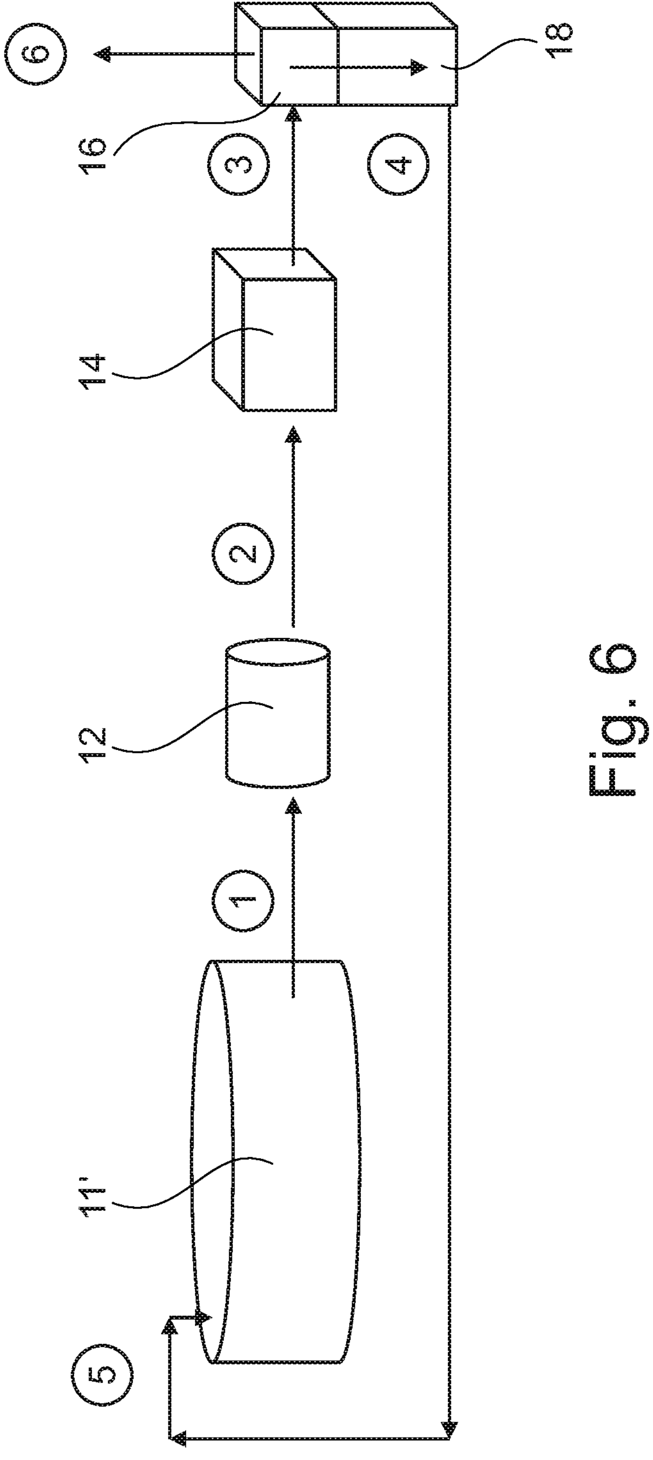
FIG. 6 shows a system where systems for measuring gases can be used in an arrangement at a RAS facility.

FIG. 6 shows an embodiment where the system or method according to the invention is used in several places in a typical RAS facility. It is shown schematically in the figure how liquid from the farming tank 11' is transferred to a drum filter 12, then to a biofilter 14 and then to a $CO_2$ aerator 16/18 and back to the farming tank 11'. In the transfer between each of these units, and also from the $CO_2$ stripper where gases leave the system, one can use a metre according to the present invention to measure the concentration of gases present in the liquid. In an aquaculture installation, it is first and foremost relevant to measure the concentration of the gases $H_2S$, $CO_2$ and $O_2$.

Thus, the system according to the invention can measure the amount of gases in the liquid that is introduced into the installation in point 5 in FIG. 6. In point 1 the level of gases in the liquid is measured out of the farming tank 11', and the changes in the level between points 1 and 5 indicate the change of quantities of gas which have occurred in the farming tank 11'. Furthermore, the system according to the invention can be arranged between different components in the RAS facility, as indicated by points 2, 3 and 4. The system in point 6 can measure amounts of gases emitted from the RAS facility. In this way, one can therefore identify whether the biofilter has accumulated too much organic material so that it starts producing $H_2S$. If the level of $H_2S$ rises, the breeder can start necessary measures.

Figure 7:
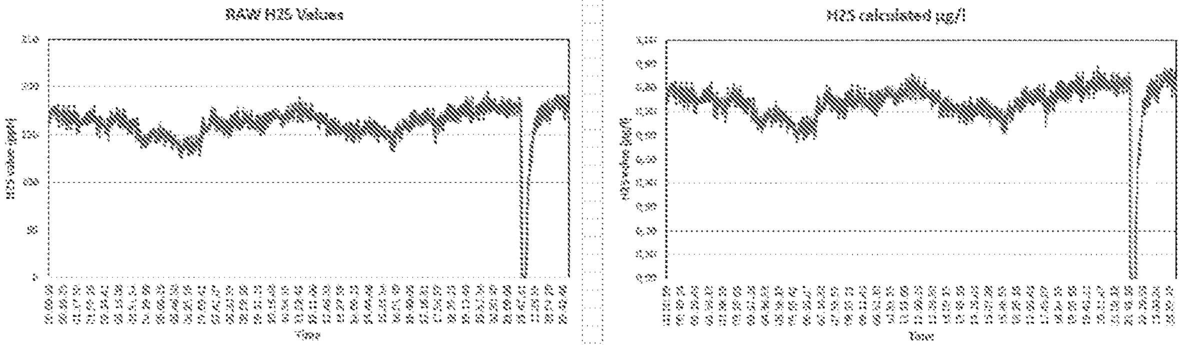
FIG. 7 shows measurements of $H_2S$ and $CO_2$.

FIG. 7 shows a plot of gases measured in ppb and converted data in mg/I based on equilibrium considerations, measured with the system according to the invention.

The following calculations which convert ppm to e.g., mg/I is based on the Dickson and Millero (1987) report.

The following calculations have been used:

$$\ln Ko'=-60,2409+9345,17/T+23,3585 \ln (001T)+S [0,023517-0,023656 (0,01T)+0,0047036 (0,01T)^2$$

where T is temperature in ° K and S is salinity.

The salt concentration of seawater is defined by salinity, given in g/kg seawater, or in Too. Probably the best data has been reported by Millero and Roy (1997); these values for the temperature range of 0 to 40° C. and the salinity range of 0 to 40%$_0$ are shown in FIGS. 9.1 to 9.4 and in Table 9.1 (shaded column to the right). The seawater values (at S=35%$_0$) are in practice similar to the values published by Weiss (1974) and by Mehrbach et al. (1973), as reported by Dickson and Millero (1987):

$$\ln Ko'=-60,2409+9345,17/T+23,3585 \ln (0,01T)++S [0,023517 -0,023656 (0,01T)+0,0047036 (0,01T)^2 \quad (9.26)$$

$$pK1'=3670,7/T-62,008+9,7944 \ln T-0,0118 S+0,000116 S^2 \quad (9.27)$$

$$pK2'=1394,7/T+4,777-0,0184 5+0,000118 S^2 \quad (9.28)$$

($K_o'$: Weiss, 1974), ($K_1'$,$K_2'$: Mehrbach et al. (1973), reported by Dickson and Millero (1987).

The salinity values S are related to the originally used chlorine values, i.e., the concentration of chloride (+ bromide and iodine, also given in g/kg or %$_o$), by:

$$S=1,80655 \text{ Cl} \quad (9.29)$$

The solubility product of calcium carbonate differs from the two different types of crystalline, calcite and aragonite. FIGS. 9.5 and 9.6 show values at specific temperatures and salinities.

FIG. 7 shows a plot of data recorded from this type of sensor. The figure shows a concentration of $H_2S$ in gas of 200 ppb. Based on theory and estimated empirical factors, this gives an $H_2S$ concentration in water of around 290 ng/litre. This is a level which is below what the known methods can detect, and the method according to the invention is thus far more sensitive as it can measure lower levels of $H_2S$ dissolved in liquid than solutions according to the prior art. It is crucial for a fish farm installation to be able to follow the development of $H_2S$, so that measures can be implemented when the amount of $H_2S$ dissolved in the water in the net cage increases, or exceeds a given predetermined threshold value.

In the sensor box 200, conventional $H_2S$ sensors can be used to measure the amount of $H_2S$ gas in a gas phase. For example, sensors from Spec Sensors (www.spec-sensors.com) that are electrochemical sensors can be used.

The invention claimed is:

1. A system for determining the amount of a gas dissolved in a liquid (10), wherein the system comprises means for continuously supplying said liquid to an equilibrator (80) arranged for adjusting the equilibrium between gases in a gas phase (80*a*) and a liquid phase (80*b*), and where gases from the gas phase in a closed gas volume are brought into contact with the liquid phase (80*b*), and where a sensor device (200) measures the amount of gas in the gas phase (80*a*), wherein the system further comprises a gas conveyor arranged to transport gases from the gas phase (80*a*) to the liquid phase (80*b*), wherein the gas conveyor is an ejector (100') and the ejector is placed in the liquid phase 80*b*) of the equilibrator (80), and wherein gases from the gas phase (80*a*) are sucked into the ejector (100') via a pipeline (100).

2. The system according to claim 1, wherein the equilibrator has an outlet (70) with a water lock for regulating the liquid level in the equilibrator (80).

3. The system according to claim 1, wherein gases from the gas phase are circulated in a closed circuit through the liquid phase (80*b*).

4. The system according to claim 1, wherein the system comprises a closed loop (200*a*) and that gases from the gas phase (80*a*) are transported by a pump (202) to the liquid phase (80*b*) via this loop (200*a*), and that a sensor device (200) is arranged in the loop (200*a*) and measures the amount of one or more gases in the gas phase (80*a*).

5. The system according to claim 1, wherein gas from the gas phase (80*a*) is led in a closed circuit via a sensor device (200) for measuring the amount of a given gas.

6. The system according to claim 1, wherein a foam dampener (120) is arranged in the equilibrator (80) in the gas phase (80*a*), wherein the foam dampener (120) is arranged in the equilibrator (80) so that there is a gas phase (80*a*) above the foam dampener (120).

7. The system according to claim 1, wherein the measurements of the amount of gas are calibrated with measurements of a gas mixture with a known gas composition.

8. A method for determining the amount of a gas dissolved in a liquid wherein the liquid (10) is continuously supplied in a closed circuit to an equilibrator (80) arranged to adjust an equilibrium between the gases in a gas phase (80*a*) and the gases dissolved in a liquid phase (80*b*) in the equilibrator (80), and where gases from the gas phase (80*a*) in a closed gas volume are brought into contact with the liquid phase (80*b*), and that a sensor device (200) measures the amount of one or more gases in the gas phase (80*a*), wherein a gas conveyor causes circulation of gases from the gas phase (80*a*) to the liquid phase (80*b*), wherein the gas conveyor is an ejector (100') and the ejector is placed in the liquid phase (80*b*) of the equilibrator (80), and wherein gases from the gas phase (80*a*) are sucked into the ejector (100') via a pipeline (100).

9. The method according to claim 8, wherein gases from the gas phase (80*a*) are transported by a pump (202) to the liquid phase (80*b*) in a closed loop (200*a*), and that the sensor device (200) is set up in the loop (200*a*) and measures the amount of one or more gases in the gas phase (80*a*).

10. The method according to claim 8, wherein the sensor device (200) measures the amount of one or more gases selected from hydrogen sulphide, carbon dioxide, oxygen and ammonia.

11. The method according to claim 8, wherein the through flow speed and the amount of liquid through the equilibrator is measured or calculated, so that the absolute amount of gas dissolved in the liquid (10) can be calculated.

12. The method according to claim 8, wherein the gas conveyor generates microbubbles to the liquid phase (80*b*).

13. The method according to claim 8, wherein the measurements are carried out in real time, and that a transmitter unit on the sensor device (200) sends data to a control unit.

14. The method according to claim 8, wherein a system is set up with valves so that one, at programmable intervals, can couple in a calibration gas with known concentrations to control drift of the sensor device (200).

15. The method according to claim 8, wherein the sensor device measures the amount of hydrogen sulphide.

* * * * *